United States Patent [19]
Beck

[11] Patent Number: 5,196,244
[45] Date of Patent: Mar. 23, 1993

[54] DISPOSABLE TISSUE TRAP WITH ASEPTIC BARRIER

[75] Inventor: William C. Beck, Sayre, Pa.

[73] Assignee: Donald Guthrie Foundation for Medical Research, Inc., Sayre, Pa.

[21] Appl. No.: 614,001

[22] Filed: Nov. 13, 1990

Related U.S. Application Data

[63] Continuation-in-part of Ser. No. 524,659, May 17, 1990, abandoned, which is a continuation of Ser. No. 326,373, Mar. 20, 1989, abandoned.

[51] Int. Cl.$^5$ ............................................. B29D 22/00
[52] U.S. Cl. ...................................... 428/35.2; 2/158; 15/209.1; 206/438; 424/443; 428/249; 428/284; 428/286; 428/913
[58] Field of Search ............... 428/171, 172, 284, 286, 428/249, 913, 35.2; 424/443; 206/438; 15/209 R; 2/158

[56] References Cited

U.S. PATENT DOCUMENTS

| | | | |
|---|---|---|---|
| 3,629,048 | 12/1971 | Davison | 161/57 |
| 4,147,580 | 4/1979 | Buell | 156/291 |
| 4,332,253 | 6/1982 | Schoots | 128/287 |
| 4,425,126 | 1/1984 | Butterworth et al. | 604/366 |
| 4,551,143 | 11/1985 | Cook et al. | 604/371 |
| 4,738,847 | 4/1988 | Rothe et al. | 428/249 |
| 4,767,825 | 8/1988 | Pazos et al. | 525/408 |

FOREIGN PATENT DOCUMENTS 2085356 11/1980 United Kingdom.

OTHER PUBLICATIONS

Aseptic Barriers-Beck and Carlson-Archives of Surgery-Aug. 1963-vol. 87, pp. 288-296.
Hand-to Hand Transmission of Rhinovirus Colds-Gwaltney et al., Annals of Internal Medicine-vol. 88, No. 4, Apr. 1978.
"False Faith in the Surgeon's Gown and Surgical Drape"-The American Journal of Surgery, vol. LXXXIII, No. 2, pp. 125-126-Beck et al.
"Reviews and Commentary—Rhinovirus Transmission"-Gwaltney et al.-American Journal of Epidemiology-May 1978, vol. 107, pp. 357-361.
"The Numbers and the Sites of Origin of the Droplets Expelled During Expiratory Activities":-J. P. Duguid-Edinburgh Medical Journal-Nov. 1945, pp. 385-401.
"How Bacteria Get from Here to There: The Basics of Surgical Asepsis"-William C. Beck-Infections In Surgery-Apr. 1985, pp. 239, 267.
"Evaluation of Virucidal Compounds for Inactivation of Rhinovirus on Hands":-Hendley, et al.-Antimicrobial Agents and Chemotherapy-Nov. 1978, pp. 690-694.

Primary Examiner—James J. Bell
Attorney, Agent, or Firm—Ralph R. Barnard

[57] ABSTRACT

The discovery of this invention is that the use of an aseptic barrier in the form of a layer of material which is impervious to the passage of water in combination with at least one layer of absorbent tissue in the form of a disposable tissue or handkerchief can function to reduce materially the transfer of pathogens such as viruses and bacteria from the bodily internal products, mucous and fluid effluent from inside a person to his hand. The above principles may be embodied in a disposable tissue including an aseptic barrier or in a method of entrapping nasal secretions in such a way that contamination of the environment from infected noses be avoided. This is accomplished by the creation of a trap in the form of a mitten-like bag, resistant to the passage of aqueous liquids, with facial tissue affixed to the outside of this mitten-like bag.

10 Claims, 4 Drawing Sheets

DISPOSABLE TISSUE TRAP WITH ASEPTIC BARRIER

CROSS REFERENCE TO RELATED APPLICATIONS

This application is a continuation-in-part of copending application Ser. No. 07/524,659, filed May 17, 1990, now abandoned, which is a continuation of application Ser. No. 07/326,373, filed Mar. 20, 1989, now abandoned.

FIELD OF THE INVENTION

This invention relates to aseptic barriers and more particularly to a method and product for providing a natural and synthetic tissue with an aseptic barrier inner layer which may be used as a handkerchief.

BACKGROUND OF THE INVENTION

The aseptic barriers in surgical medical field are well known. They take the form of rubber gloves, gowns, masks, drapes, as well as wrappers for materials which have been subjected to sterilization. An aseptic barrier has been defined as a material placed between an aseptic area, such as an operative incision, and areas which harbor microorganisms with the purpose of preventing the spread of bacteria into the sterile zone. Such a definition was included in an article "Aseptic Barriers" which the present inventor authored with Warner W. Carlson, which was published in Archives of Surgery, August 1963, Vol 87 pp 288-296, a publication of the American Medical Association. "How Bacteria Get from Here to There: The Basics of Surgical Asepsis", was also written by the present inventor and was published in Infections in Surgery, April 1985, pp 239 and 267. As identified in these articles moisture in the material will allow bacteria to be transmitted through the material. Stated more broadly, bacteria are transported from one area to another by some vehicle such as dust, water, or a human or other animate vector. When we consider bacterial "strike through" in relation to aseptic barriers, the transmission by a vehicle, rather than motility per se, is the factor of major importance. It is, therefore, imperative that a barrier material be impervious to bacterial vehicles such as water, if it is to be effective.

Another article co-authored by the present inventor relating to the need for aseptic barriers and that the aseptic barrier be impervious to the passage of water, is an editorial that appeared in the February 1952 edition of the American Journal of Surgery, Vol LXXXIII, No.2 pages 125-126.

The only mode of transfer of viruses, bacteria or other pathogens is by being carried by air or gaseous medium either by droplets of air or strike through. The transfer of pathogens from person to person is known to frequently occur from hand to hand contact. This is particularly true in the case of the common cold.

The common cold is often, if not usually, caused by one of the rhinoviruses, of which there were, a decade ago, at least 89 distinct serologic types with at least one subtype recognized. Thus it is improbable that any vaccine will become available.

Furthermore, there are at present no known antivirals to these rhinoviruses, and very little effort is being expended upon such a discovery; nor is there much hope of finding one. It appears that our only defense against the common cold is the prevention of its spread.

This implies an intimate knowledge of the mechanisms of its spread. This would be followed by a logistically and economically feasible method of its interruption. I believe that the latter is both mechanically even profitably possible.

Gwaltney and Hendley have shown that the rhinovirus is spread principally if not only through the nasal mucus membrane, in a series of articles: 1) Hendley J. O., Mika L. A., Gwaltney J. M. Jr: Evaluation of Virucidal Compounds for Inactivation of Rhinovirus on Hands, Antimicrob. Agents Chemother. Vol 14. NO. 5:690-694, 2) Gwaltney, J. M., Jr. and J. O. Hendley. 1977 Rhinovirus transmission: One if by Air, Two if by Hand. Trans. Am. Clin. Climatol Assoc. 89: 194-200, 3) Gwaltney, J. M., Jr. P. B. Moskalski, and J. O. Hendley. 1978. Hand to Hand Transmission of Rhinovirus Colds. Ann. Intern. Med. 88:463-467. The common cold is a nose-to-nose (or nose to eye) disease. It is from nose to hand, by handshake to another hand to another nose transmission.

The obvious potential source, the transmission of the virus by droplets or droplet nuclei either does not or very rarely takes place. The droplets of sneeze contain little if any nasal secretion. This was beautifully demonstrated by Duguid of the Department of Bacteriology in (Edinburgh, J. P. Duguid. 1945. The Numbers and the Sites of Origin of the Droplets Expelled During Expiratory Activities. Edinburgh Medical Journal 52:385-401). In 1897 and in 1899 Flugge demonstrated that small droplets are often emitted from the mouth during a variety of expiratory activity. Normal breathing, sneezing, coughing, speaking and laughing produce microbe-laden droplets. A variety of methods have been employed to demonstrate and even count the droplets, so that it has been shown that a sneeze may produce from a few hundred thousand to a few million droplets. Droplets larger and 100 microns rapidly drop to the floor. Smaller droplets evaporate before reaching the floor, and through evaporation form residues of "droplet nuclei" which may contain viable microorganisms, an, like smoke, may remain airborne for hours or even days.

But Duguid proved that nearly all of the droplets in sneezing or talking have the salivary pool in the front of the mouth as their source. There is little if any contribution from nasal secretions. A single cough may produce droplets from the throat, but mostly from the front of the mouth (again the salivary pool), ranging in number from a few hundred to many thousand with content from the front of the mouth and the fauces.

Gwaltney and Hendley quote the work of several authors who have shown the nose and even the eye were splendid portals of entry for respiratory viruses with minute doses producing the infection. They concluded that contamination of the hands of the infected individual, hand-to-hand contact with a new host by contaminated fingers would spread the infection.

Furthermore, they showed that nose blowing resulted in the contamination of the hands. They recovered virus from half of the hands of persons with natural or experimentally induced colds with a single sampling, and in 90 percent with repeated sampling. On the other hand, virus was found in the saliva of only half of infected persons, and then only in low titer. No large volume titers were produced by sneezing and coughing by infected volunteers with experimental colds. Also close contact between coughers and sneezers did not cross infect normals. Yet a ten second hand-to-hand contact resulted in demonstrable transfer in 20 to 28 exposures. Furthermore, virus on the recipient hand led to infection in eight of nine instances when the contaminated finger was deliberately placed in contact with the mucosa in the nose.

Facial tissue, such as "KLEENEX TM ", poses no barrier to the contamination of the hands no matter how many layers are used. This has been demonstrated in surgical barriers, and has also shown how microorganisms progress from one site to another.

Hendley, Mika, and Gwaltney have suggested the use of a virucide, such as alcohol, on the hands. The problem with using virucide is that it would be bulky to carry around at all times when a person might need to blow his/her nose. If a dispenser of virucide was not around it is quite possible and in fact probable that most individuals would forego using it. The pathogens should be prevented from coming into contact with the hand of the infected individual in the first place. Thus there is little or no protection for the person who comes into contact with a facial tissue that has been used by an infected individual to blow his nose.

Stated simply, the use of handkerchiefs and paper tissues which transfer the noxious agent from the discharges from a person's nose to his hands continues without exception and via the receptors hand to his nose.

While the relationship between an aseptic barrier and the fact that such barrier must be impervious to the passage of water or any kind of aqueous solution is known in the art, heretofore, it has been unrecognized that these principles have application to the transfer of viruses and bacteria from person to person.

SUMMARY OF THE INVENTION

The method of spread of the common cold is such that it lends itself to a simple solution. This is the creation of a facial tissue which is impermeable to the passage of liquids and thus will prevent contaminants from reaching the fingers of the carrier. When this is accomplished, spread to a second potential victim be prevented.

The discovery of this invention is that the use of an aseptic barrier in the form of a layer of material which is impervious to the passage of water in combination with at least one layer of absorbent tissue in the form of a disposable tissue or handkerchief can function to reduce materially the transfer of pathogens such as viruses and bacteria from the bodily internal products, mucous and fluid effluent from inside a person to his hand.

The present invention teaches that bacterial transfer from person to person can be avoided by creating a handkerchief where water resistant material acts as a barrier against at least one layer of absorbent material. Further, the present invention teaches that the material providing the moisture resistant barrier (to prevent bacterial transfer from person to person) can be bonded on at least one side to the material providing a moisture absorbent quality.

The above principles may be also be embodied in a method of entrapping nasal secretions in such a way that contamination of the general environment can be avoided. This is accomplished by the creation of a trap in the form of a mitten-like bag wherein the material forming the bag is impervious to the passage of aqueous liquids, with facial tissue affixed to at least a portion of the outside of the bag. The user inserts his hand into the bag, and then blows his nose into the facial tissue on at least a portion of the outer side of the bag. The user grasps a portion of the bag with his fingers or thumb inside of the bag and grasps and removes his hand such that the bag is turned inside out, thereby trapping any pathogens inside of the inverted bag. It can now discarded, thus keeping contaminated nasal secretions isolated.

It is accordingly a primary object of the present invention to provide a new and improved method for preventing the transfer of harmful pathogens form the bodily internal products, mucous and fluid effluent from inside a person to this hands.

A further object of the present invention, is to provide a new and improved tissue product for preventing the transfer of harmful pathogens from the bodily internal products, mucous and fluid effluent from the cagier's nose to his hands.

A further object of the present invention, is to provide a new and improved tissue product with aseptic barrier including a layer of material which material is impervious to the passage of water therethrough and a layer of liquid absorbent material on at least one side of the layer of material which is impervious to the passage of water therethrough for preventing the transfer of harmful pathogens from the bodily internal products, mucous and fluid effluent from inside a person to his hands.

A further object of the present invention, is to provide a new and improved handkerchief including a barrier internal therein which prevents water and aqueous solution strike through from one side to the other.

A further object of the present invention, is to provide a new and improved tissue product for preventing the transfer of harmful pathogens from the bodily internal products, mucous and fluid effluent from inside a person to his hands and for entrapping nasal secretions in such a way that contamination of the environment from infected noses be avoided.

A further object of the present invention, is to provide a new and improved tissue product which creates a trap in the form of a mitten-like bag, resistant to the passage of aqueous liquids, with facial tissue affixed to the outside of this mitten-like bag.

These and other objects, features and advantages of the present invention should become apparent from the following description when taken in conjunction with the accompanying drawings.

DETAILED DESCRIPTION OF THE PREFERRED EMBODIMENT

The teachings of the present invention suggest that the hand can be protected from contamination by the provision of a barrier between the hand and the contamination source through the insertion of a waterproof pliable plastic material between the layers of the facial tissue.

Figure 1:
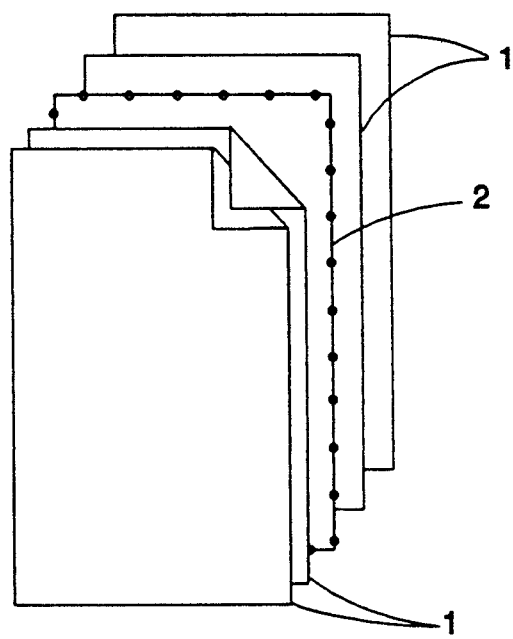
FIG. 1 shows the layered disposable tissue or handkerchief in accordance with the present invention wherein layer 2 is impervious to the passage of water or aqueous solution and layers 1 on both sides of the layer 2 are made from material which absorbs water and aqueous solution.
Figure 2:
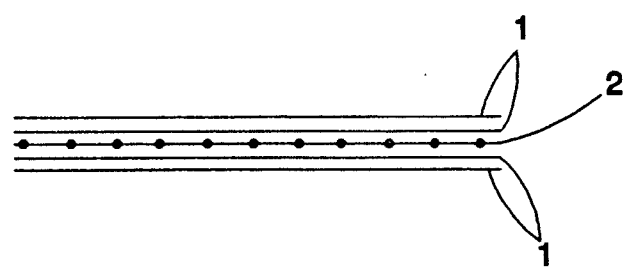
FIG. 2 shows a top view of layers of FIG. 1 wherein, the layer 2 is impervious to water and is differentiated by the small circles signifying a different function than the outer layers.
Figure 3:
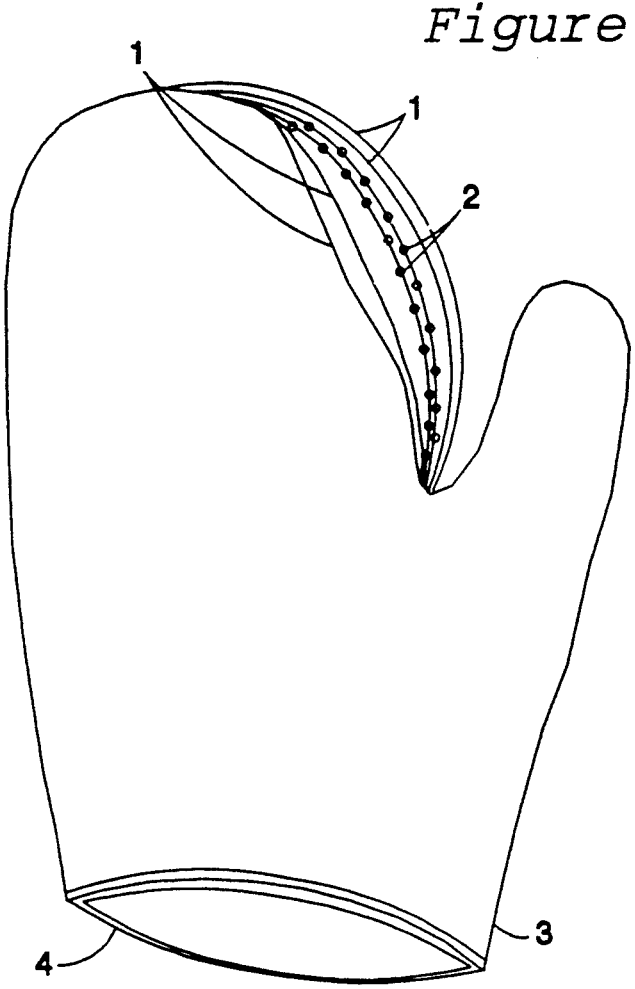
FIG. 3 shows a tissue in the form of a mitten-like bag made in accordance with the teachings of the present invention wherein layer 2 is formed as a bag and is impervious to the passage of water or aqueous solution and layers 1 on both sides of the layer 2 are made from material which absorbs water and aqueous solution.
Figure 4:
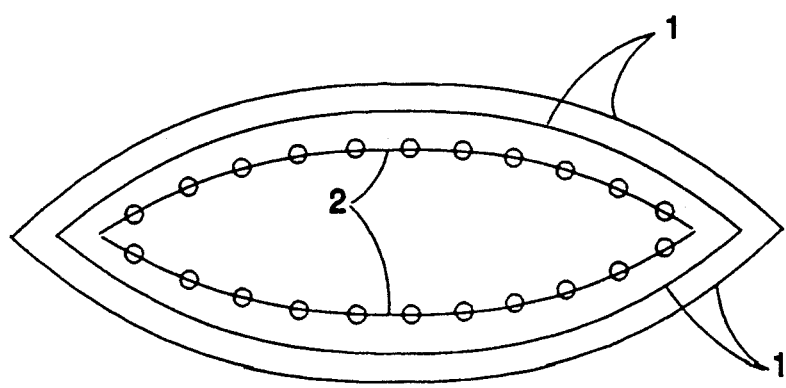
FIG. 4 shows a bottom view of layers of FIG. 3.

A large variety of very thin, pliable materials (e.g. polyethylene) are available, which will not impair either the flexibility, nor the softness of the tissue. In the embodiments shown in FIGS. 1 and 2, the plastic would simply be incorporated between the layers of the tissue and held in place by embossing; which is presently employed to hold the layers of tissue together. This is a simple, easily manufactured, and inexpensive method of protecting the hands from contamination. In the embodiment shown in FIGS. 3-6, the plastic could be formed in the shape of a mitten-like bag 3 and tissue 1 is affixed to at least a portion of the outside of the aseptic barrier layer 2.

In the field of surgery and medicine aseptic barriers are mandated by the Office of Safety Health Administration (OSHA), to prevent contamination by body fluids in hospitals (Universal Precautions (8)) These aseptic barriers are required to be resistant to the passage of liquids.

I propose the same quality for those facial tissues which are to be used to blow one's nose, when afflicted with a common cold. These liquids are as contagious as those contaminated by other more serious, and disabling disease.

However, as facial tissues are used for many purposes other than for blowing the nose, I would furthermore propose that liquid impermeable tissues could be labeled as such. This would enable the manufacturer to produce facial tissue particularly suited for the victim of the common cold, even permitting the manufacturer to incorporate emollients in the tissue, as is presently being done with certain tissues.

Figure 5:
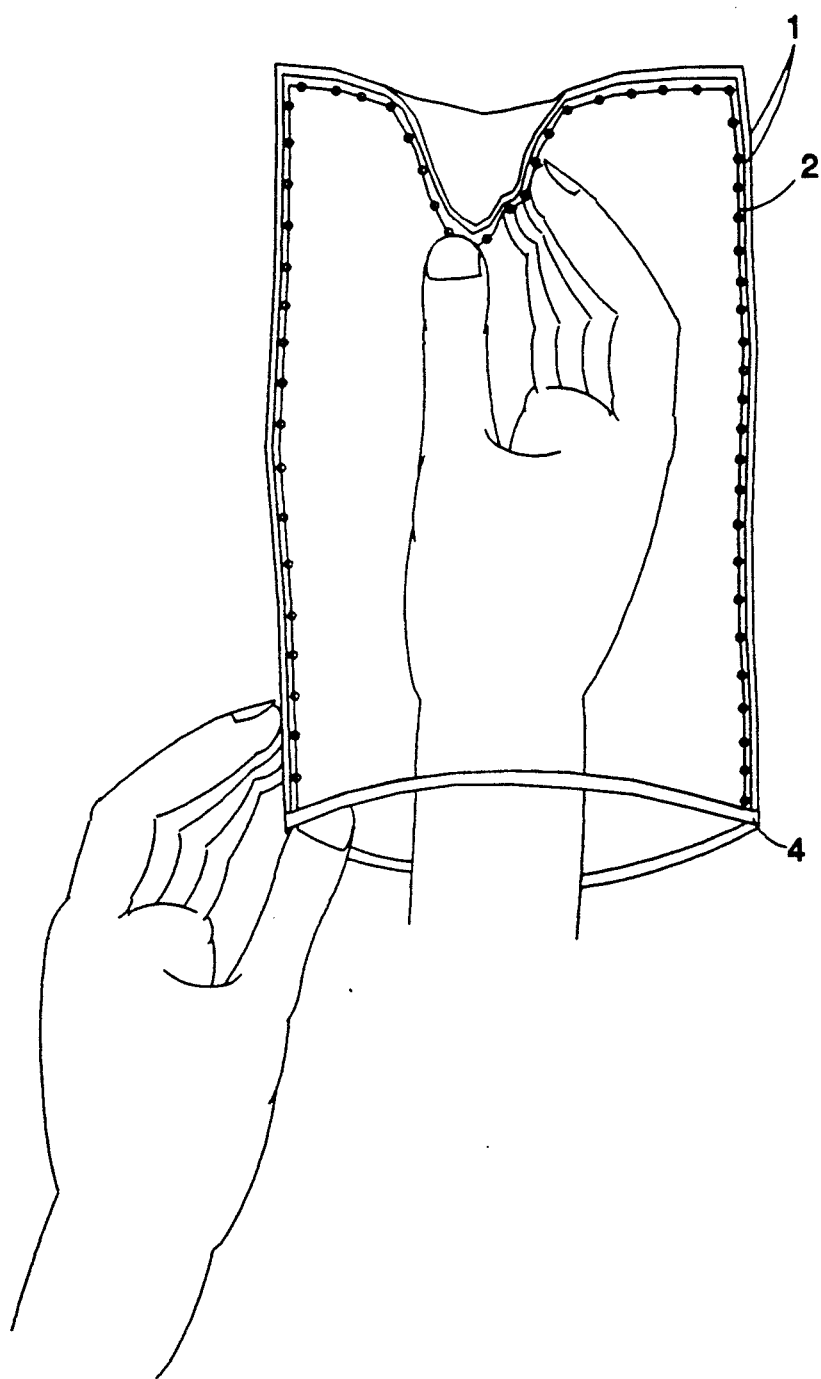
FIG. 5 shows a tissue in the form of a bag wherein the user is inverting the bag as it is removed in accordance with the teachings of the present invention.

The above principles may be also be employed in a method of entrapping nasa secretions in such a way that contamination of the environment from infected noses is avoided. This is accomplished by the creation of a trap in the form of a mitten-like bag, resistant to the passage of aqueous liquids, with facial tissue affixed to at least a portion of the outside of this mitten-like bag, as shown in FIGS. 3-6. The bags could be constructed in a variety of shapes and the bags need not include a thumb portion, as shown in FIG. 5. Moreover, the means for the hand attaching to the interior end of the bag in order to turn the bag inside out can include a tab (not shown) or may be accomplished by using the thumb and fingers to secure the inside of the bag during the reversing process. The user will insert his hand into the bag, and then blow his nose into the facial tissue on the outer side of the bag.

Figure 6:
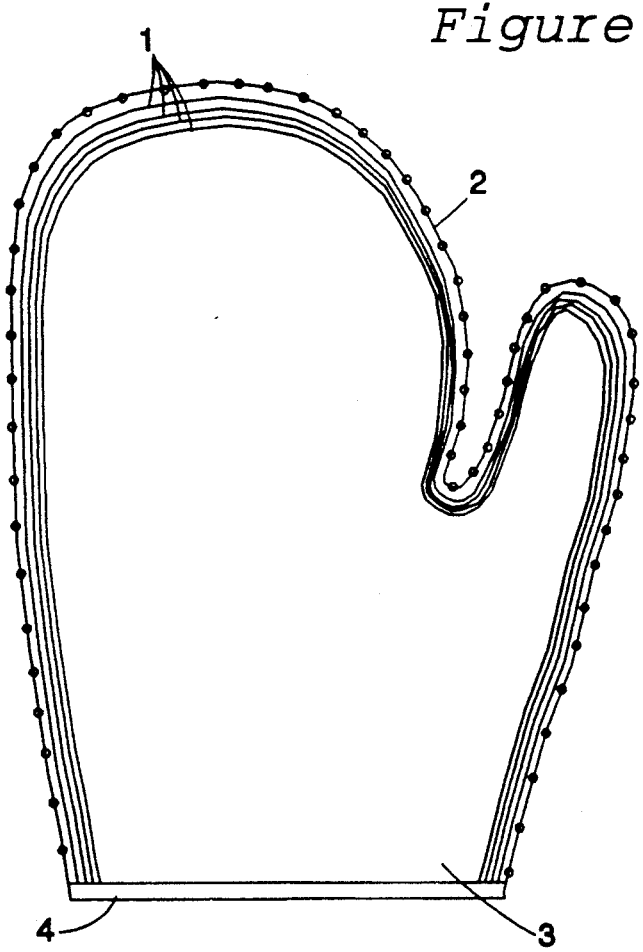
FIG. 6 shows a tissue as in FIG. 3 wherein the bag has been inverted thereby trapping the contaminated water absorbent layer inside the inverted bag.

As shown in FIG. 5, the user grasps the inside of the bag with his fingers or thumb inside of the bag and grasps the bottom edge of the bag with his other hand and removes his hand such that the bag is turned inside out, thereby trapping any pathogens inside of the inverted bag. It can now be discarded, thus keeping contaminated nasal secretions isolated. The bottom edge of the bag could include a specific identification of a sterile spot, inside or outside of the bag, where the user's free hand could grasp to aid in removing the bag such that the both of the user's hands would remain sterile. It is also possible to use this contrivance to protect the air from droplet contamination from droplets emanating from a cough or sneeze. Furthermore, it is possible to incorporated a seal through an adhering material to the inner surface of the plastic trap liner, so that a permanent isolation of the contaminated material can be obtained. As shown in FIG. 6, the bag 3 includes sealing means 4 and has been inverted and sealed.

In this day, were Institutional Universal Precautions for body fluids of patients is mandated by OSHA regulation, this trap for nasal secretions can be of value in protection of attendants. Because of the added advantages of the tissue including an aseptic barrier in the form of a mitten-like bag, it is the preferred embodiment of the present invention.

The nature of the layers of the material can vary over a wide range providing the internal layer 2 is impervious to water and aqueous solution generally and the outer layers are basically soft and absorbent of water and aqueous. It is important however, that the layers adhere together so that they stay together during the time they perform their function such as wiping ones nose and there is no danger of strike through from one side to the other of aqueous effluent moisture thereby transporting bacteria or viruses etc., with the sure result that the person's hands become animate vector for the bacteria or virus moving to another person's hand or other body part.

The method of adhering one layer to the another can be accomplished in a number of ways such as:
a. the use of an embossing technique;
b. the use of an adhesive material;
c. The use of a double-sided tape around the periphery of each layer to hold them together; and
d. the bonding of the materials with heat, a solvent and/or pressure.

The types of materials that can be used for the layer that is impervious to the passage of moisture or other aqueous solutions can be as varied as the material used in disposable diapers, and probably some material that would not function as well as in a diaper. These material include a cellulose such as cellophane, polymers such as polyethylene and saran, and rubber such as latex, as well as compositions of synthetic or natural fibers which include water proofing additives both natural and synthetic.

The material used for the absorbent layers can vary widely and include all of those materials which might be used in baby diapers, including textile and paper products and including tissue of the kind that are in facial tissues now on the market. The important point is that the liquid impervious layer be interposed between two liquid absorbent layers on both sides in a manner so it does not slip and slide away from providing the barrier against moisture strike through as desired. Of course, the user of the especially made tissue made in accordance with the teachings of the present invention must be aware that he must not manipulate the tissue so that one side thereof which is isolated from the other side thereof when he uses the same.

As used herein the words "layer of material" can mean plural layers of materials. For example, as shown in the drawing the absorbent layer on each side of the impervious layer is in fact shown as more than one layer.

The function of sealing means 4 as shown in FIGS. 5 and 6 can be accomplished in a number of different embodiments known to those skilled in the art of sealing aseptic barriers. For example, sealing means 4 could be an adhesive strip, a locking seal (as in ZIPLOC TM bags), or any other means that provides an adequate seal within the scope and teachings of the present invention.

The shape of the aseptic barrier 2 shown in FIGS. 3-6 formed as bag can be in a variety of shapes provided that the user's are still protected. The function that needs to be maintained is that the user's hand must be able to grab hold of the inside of the bag so that the bag may be turned inside out with ease. A tab might be used on the far interior end of the bag for the purpose of grabbing hold of the same. Ultimately, the fingers and thumb in the bag can just tighten on the interior end of the bag for the reversing process. While a mitten shape is shown, the aseptic barrier could be in the shape of a glove, rectangle, oval or any other shape within the scope and teachings of the present invention.

The foregoing description has been directed to particular embodiments of the invention in accordance with the requirements of the Patent Statutes for the purposes of illustration and explanation. It will be apparent, however, to those skilled in this art that many modifications and changes will be possible without departure from the scope and spirit of the invention. It is intended that the following claims be interpreted to embrace all such modifications.

I claim:

1. A handkerchief, for wiping or covering the nose, mouth or hands in a manner such that any pathogenic bacteria or virus present in the fluid transferred to the tissue are not further transmitted to the user's hands, comprising:
   a. an aseptic barrier, formed of material which is impervious to the passage of water carrying pathogenic bacteria or virus therethrough and is in the form of a bag such that the user's hand can fit inside of said bag; and
   b. a layer of liquid absorbent material on and at the outside of said aseptic barrier formed as a bag.

2. The article of claim 1, wherein said aseptic barrier formed as a bag can be turned inside out such that said liquid absorbent material and any pathogenic bacteria or virus present in the fluid transferred to said absorbent layer are trapped inside of said inverted bag.

3. The article of claim 1, wherein said aseptic barrier formed as a bag further includes sealing means such that said aseptic barrier formed as a bag can be turned inside out and sealed such that said liquid absorbent material and any pathogenic bacteria or virus present in the fluid transferred to said absorbent layer are sealed inside of said sealed bag.

4. The method of making a handkerchief, for wiping or covering the nose, mouth or hands in a manner such that any pathogenic bacteria or virus present in the fluid transferred to one side of the tissue are not further transmitted to the user's hands, comprising a disposable tissue having an aseptic barrier to protect against the transmission of pathogenic bacteria or virus to the hands of the use and then to another person through touching, comprising the steps of:
   a. selecting material which is impervious to the passage of water carrying pathogenic bacteria or virus;
   b. forming said material impervious to the passage of water into a bag and to a size of material such that the user's hand can fit inside said bag and said bag is usable as a handkerchief; and
   c. adhering liquid absorbent material on the outside of said water impervious material formed into a bag.

5. The method of claim 4 further including providing sealing means on said bag for sealing said bag after it has been turned inside out such that said liquid absorbent material and any pathogenic bacteria or virus present in the fluid transferred to said absorbent layer are sealed inside of said sealed bag.

6. The method of claim 4 further including labeling the outside of said bag such that one can identify which side of said handkerchief is contaminated.

7. A method of using a handkerchief, for wiping or covering the nose, mouth or hands, comprising a disposable tissue having an aseptic barrier to protect against transmission of pathogenic bacteria or virus to the hands of the user and then to another person through touching, comprising the steps of:
   a. selecting a disposable tissue having an aseptic barrier, said disposable tissue having at least two layers of material, a layer impervious to the transmission of liquid in the form of a bag such that the user's hand can fit inside of said bag, and at least one layer composed of liquid-absorbent material affixed to the outside of said liquid impervious layer in the form of a bag;
   b. using said disposable tissue in a manner such that any pathogenic bacteria or virus present in the fluid transferred to the tissue cannot be further transmitted to the user's hands.

8. The method of claim 7 further comprising the steps of turning said bag inside out after said handkerchief has been used such that any pathogenic bacteria or virus present in the fluid transferred to the tissue are trapped inside of said sealed bag.

9. The method of claim 7, further comprising selecting said disposable tissue wherein said liquid impervious layer in the form of a bag includes sealing means for sealing said bag after it has been turned inside out such that said liquid absorbent material and any pathogenic bacteria or virus present in the fluid transferred to by said absorbent layer are sealed inside of said sealed bag.

10. The method of claim 9 further comprising the steps of turning said bag inside out after said handkerchief has been used, and sealing said bag such that any pathogenic bacteria or virus present in the fluid transferred to the tissue are sealed inside of said sealed bag.

* * * * *